US008600069B2

(12) United States Patent
Lee et al.

(10) Patent No.: US 8,600,069 B2
(45) Date of Patent: Dec. 3, 2013

(54) MULTI-CHANNEL ACTIVE NOISE CONTROL SYSTEM WITH CHANNEL EQUALIZATION

(75) Inventors: Ming-Ran Lee, Troy, MI (US); Takeshi Abe, Garden City, MI (US); Ming-te Cheng, Ann Arbor, MI (US); Frederick Wayne Vanhaaften, Northville, MI (US); Teik Lim, Mason, OH (US); Mingfeng Li, Cincinnati, OH (US); Jie Duan, Cincinnati, OH (US)

(73) Assignee: Ford Global Technologies, LLC, Dearborn, MI (US)

( * ) Notice: Subject to any disclaimer, the term of this patent is extended or adjusted under 35 U.S.C. 154(b) by 318 days.

(21) Appl. No.: 13/071,712

(22) Filed: Mar. 25, 2011

(65) Prior Publication Data

US 2011/0235693 A1 Sep. 29, 2011

Related U.S. Application Data

(60) Provisional application No. 61/317,769, filed on Mar. 26, 2010.

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04B 1/00*** | (2006.01) |
| ***H04R 3/00*** | (2006.01) |

(52) U.S. Cl.
USPC .......... 381/71.11; 381/86; 381/122; 381/71.1

(58) Field of Classification Search
USPC .................. 381/71.7, 71.1, 71.2, 71.9, 71.11, 381/71.12, 86, 122
See application file for complete search history.

(56) References Cited

U.S. PATENT DOCUMENTS

| | | | | |
|---|---|---|---|---|
| 2008/0144853 | A1 | 6/2008 | Sommerfeldt et al. | |
| 2009/0086990 | A1* | 4/2009 | Christoph | 381/71.12 |
| 2010/0014685 | A1* | 1/2010 | Wurm | 381/71.11 |

OTHER PUBLICATIONS

Jie Duan, Mingfeng Li and Teik C. Lim, (University of Cincinnati), Ming-Ran Lee, Wayne Vanhaaften, Ming-Te Cheng and Takeshi Abe (Ford Motor Company), Control of Powertrain Noise Using a Frequency Domain Filtered-x LMS Algorithm, SAE International, 2009-01-2145, 2009.

S.J. Elliott and J.G. Cook, Institute of Sound and Vibration Research, University of Southampton, A Preconditioned LMS Algorithm for Raid Adaptation of FeedForward Controllers, 2000 IEEE.

Sen M. Kuo, Mansour Tahernezhadi, and Wenge Hao, Convergence Analysis of Narrow-Band Active Noise Control System, IEEE Transactions on Circuits and Systems—II: Analog and Digital Signal Processing, vol. 46,No. 2, Feb. 1999.

(Continued)

*Primary Examiner* — Xu Mei
*Assistant Examiner* — Douglas Suthers
(74) *Attorney, Agent, or Firm* — Frank A. MacKenzie; Brooks Kushman P.C.

(57) ABSTRACT

A multiple error filtered-x least mean square (MEFxLMS) algorithm using a channel equalization virtual secondary path for an active noise control/cancellation (ANC) system for treating noise in a Multiple-Input Multiple-Output (MIMO) system. The channel equalization technique equalizes amplitude levels of the estimated response of all primary channels to overcome limitations caused by the frequency dependent property of standard filtered-x least mean square (FxLMS) algorithm, reduce the variation of convergence speed existed in the multiple channels, and improve the overall performance of the control system. The convergence property of the algorithm is analyzed in the frequency domain.

4 Claims, 10 Drawing Sheets

(56) References Cited

OTHER PUBLICATIONS

Jaret K. Thomas, Stephan P. Lovstedt, Jonathan D. Blotter, and Scott D. Sommerfeldt, Eigenvalue Equalization filtered-x algorithm for the multichannel active noise control of stationary and nonstationary signals, Received Aug. 9, 2007; revised Feb. 8, 2008; accepted Mar. 6, 2008.

Guo-Yue Chen, Masato Abe, and Toshio Sone, Research Institute of Electrical Communication, Tohoku University, Newport Beach, CA, USA Active 95, Jul. 6-8, 1995.

* cited by examiner

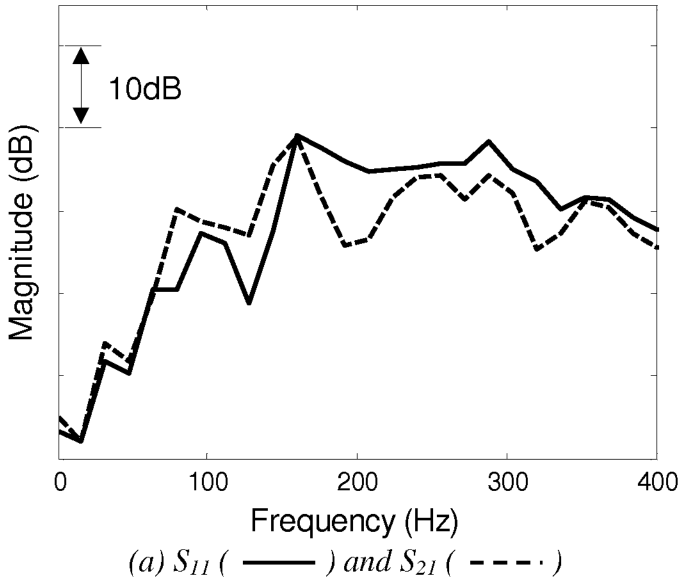
*(a) $S_{11}$ ( ——— ) and $S_{21}$ ( - - - · )*
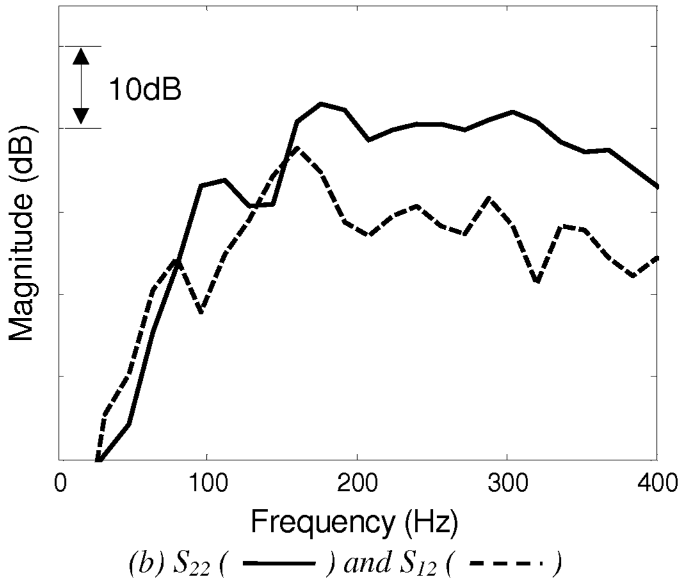
*(b) $S_{22}$ ( ——— ) and $S_{12}$ ( - - - · )*
FIG 6

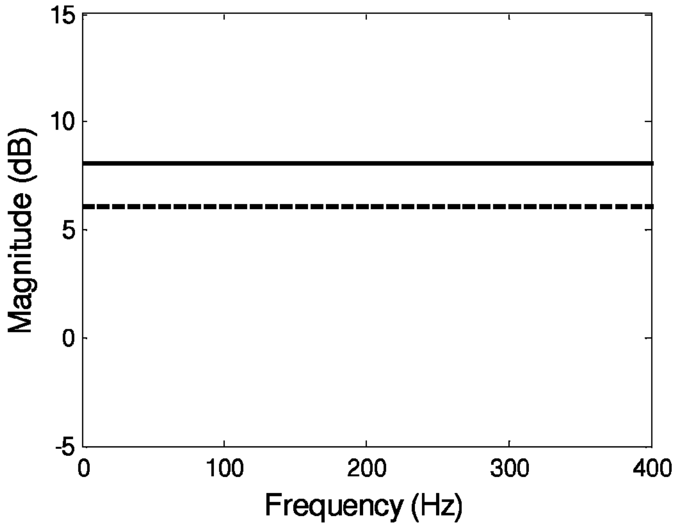
*(a)* $S_{11}^{e}$ (——) and $S_{21}^{e}$ (- - -)
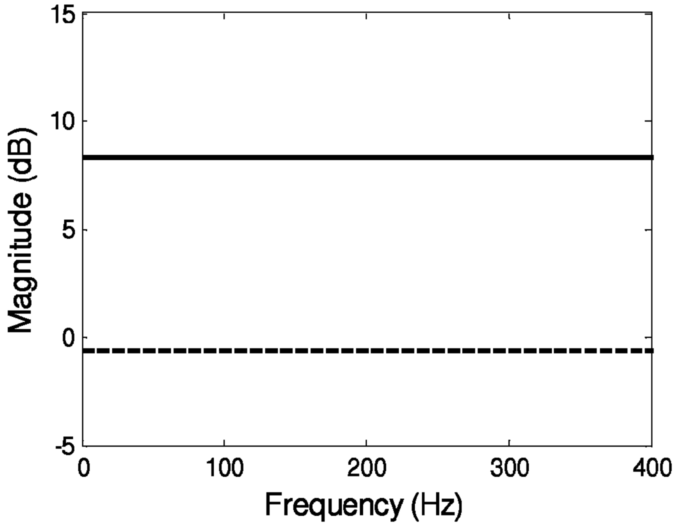
*(b)* $S_{22}^{e}$ (——) and $S_{12}^{e}$ (- - -)
FIG 7, *Magnitude responses of four virtual secondary path transfer functions in 2I2O system using improved virtual secondary path algorithm. (a)* $S_{11}^{e}$ (——) *and* $S_{21}^{e}$ (- - -); *(b)* $S_{22}^{e}$ (——) *and* $S_{12}^{e}$ (- - -).

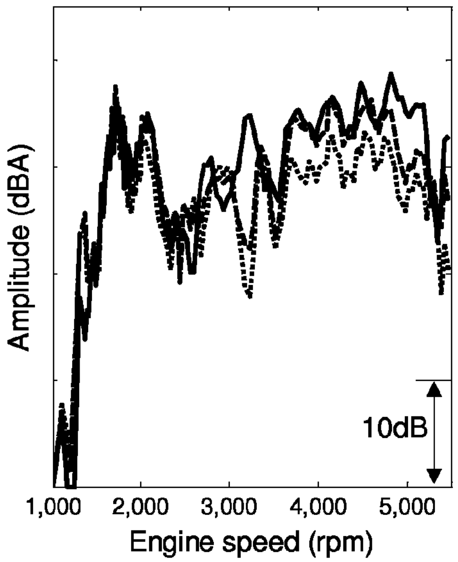
*(a) Error 1*
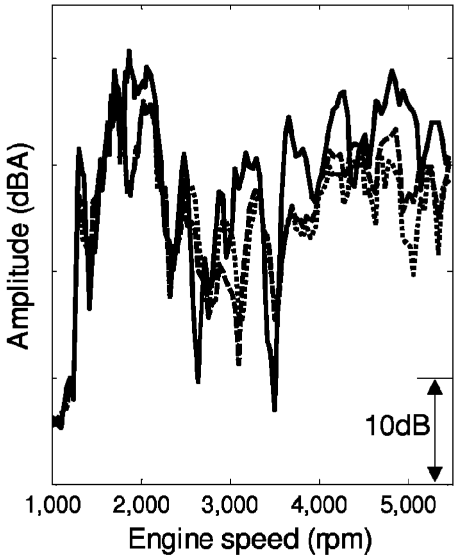
*(b) Error 2*
FIG 8. *(a) Error 1. (b) Error 2. (Keys: solid line ——, baseline noise response; dashed line - - - -, conventional EE-FxLMS algorithm; and dotted line ··········, the improved virtual secondary path algorithm)*

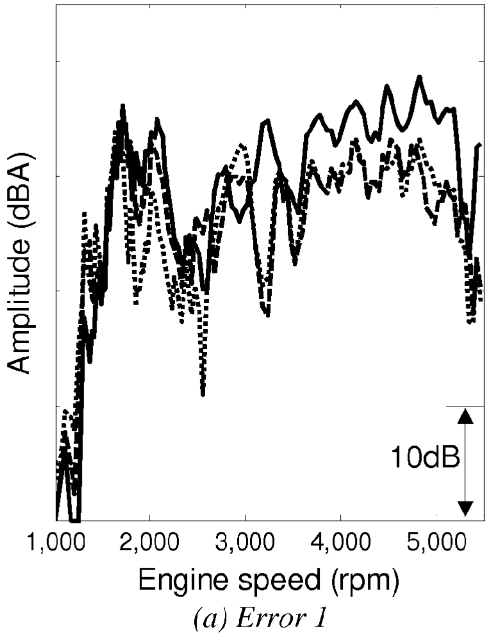
*(a) Error 1*
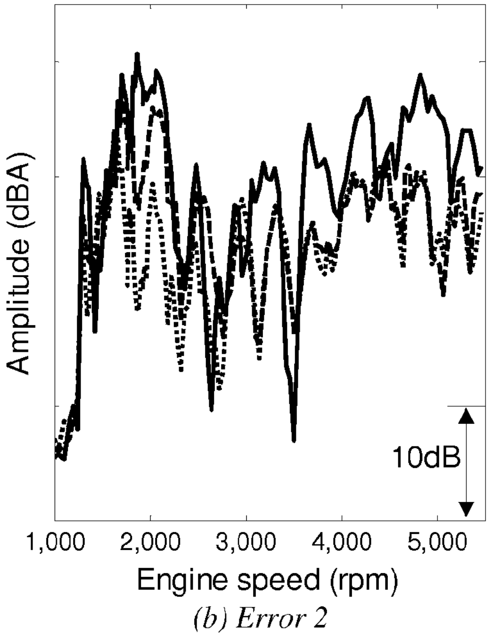
*(b) Error 2*
FIG 9. *(a) Error 1. (b) Error 2. (Keys: solid line ——, baseline noise response; dashed line – – – ·, without turning point; and dotted line ··········, with turning point)*

MULTI-CHANNEL ACTIVE NOISE CONTROL SYSTEM WITH CHANNEL EQUALIZATION

CROSS-REFERENCE TO RELATED APPLICATIONS

This application claims the benefit of U.S. provisional Application No. 61/317,769 filed Mar. 26, 2010, the disclosure of which is incorporated in its entirety by reference herein.

TECHNICAL FIELD

Noise in the cabins of automotive vehicles may be caused by several sources including powertrain, tire-to-road contact, wind, and a variety of electromechanical accessories. The powertrain noise is typically most dominant when the vehicle's engine is idling or varying in speed. These noise components, especially the powertrain noise inside the vehicle, can be annoying to the passengers and may play a major role in the perceived quality of the vehicle design. Furthermore, demands for better NVH (noise, vibration and harshness) performance requires some or all of these noise components be treated effectively.

BACKGROUND

One possible way to reduce objectionable powertrain noise is to employ an active noise cancellation (ANC) system to tune the sound perceived by vehicle occupants.

Among the considerations that are important to in the analysis of powertrain noise are: (1) powertrain noise is typically dominated by a large number of harmonics; and (2) the amplitude and frequency of each harmonic are functionally related to the rotational speed of the engine. Therefore, the frequency range of interest is fairly broad, since an automotive vehicle engine may operate over a large speed range (revolutions per minute, rpm).

The properties of the convergence are affected by the eigenvalue spread of the autocorrelation matrix of the filtered reference signal. In general, the eigenvalues of the autocorrelation matrix of the filtered reference signal are variable throughout the frequency range of interest, which leads to frequency dependent behavior of the convergence. Hence, each frequency will have its own optimal step size. To maintain system stability, the step size should be chosen based on the frequency that has the smallest optimal step size. Otherwise, the system will become unstable firstly at that frequency. This may, however, tend to degrade the overall performance of the ANC system, because the step size chosen in that way is only optimal for that particular frequency and too small for other frequency components. This may slow down the convergence speed for other frequencies and degrade the overall performance of system.

Several variations of filtered-X least mean square (FxLMS) algorithms have been suggested. A preconditioned LMS algorithm adds another filter to flatten the magnitude response from controller output to error signal. (S. J. Elliott and J. G. Cook, "A preconditioned LMS algorithm for rapid adaptation of feed-forward controllers," *Proceeding of the IEEE International Conference on Acoustics, Speech and Signal Processing* (*ICASSP'*00), Vol. 2, pp. 845-848, Istanbul, Turkey, (2000).)

To improve the convergence speed of the standard FxLMS algorithm, it has been proposed that the determinant of autocorrelation matrix should be as flat as possible. Among ways to achieve this are to adjust the positions of secondary sources (speakers) and error sensors (microphones), increase the number of secondary sources, and add an inverse filter of the secondary path. (G. Chen, M. Abe, and T. Sone, "Improvement of the convergence properties of the ANC system based on analysis in the frequency domain," *Proceeding of Active 95*, Newport Beach, Calif., pp. 1013-1024, (1995).

The amplitude of the reference signal may be chosen to be inversely proportional to the magnitude response of the secondary path at the corresponding frequency. (S. M. Kuo, M. Tahernezhadi, and W. Hao, "Convergence analysis of narrowband active noise control system," *IEEE Transactions on Circuits and Systems-II: An Analog and Digital Signal Processing*, Vol. 46, No. 2, pp. 220-223, (1999)).

It is also known to apply a frequency domain fast least mean square (FLMS) to deal with the problem of slow convergence speed. (J. Duan, et. al., "Active Control of Powertrain Noise Using a Frequency Domain Filtered-x LMS Algorithm," *Proceedings of the SAE Noise and Vibration Conference and Exhibition*, St. Charles, Ill., Paper No. 2009-01-2145, (2009)) However, such an approach increases the computational cost and/or the algorithm's complexity.

Another suggested approach is the use of an eigenvalue equalization filtered-x least mean square (EE-FxLMS) algorithm. See, for example, US Patent Application 2008/0144853A1, and "Eigenvalue equalization filtered-x algorithm for the multi-channel active noise control of stationary and non-stationary signals," *Journal of the Acoustical Society of America*, Vol. 123, No. 6, pp. 4238-4249, (2008).

The eigenvalue equalization technique flattens the response of each secondary path independently of one another and so does not properly deal with the interactions between secondary paths. This technique therefore experiences difficulties when it is applied to a multiple channel [MIMO] ANC system, especially where there are unbalanced responses of secondary paths.

It is therefore an objective of the present invention to provide a method by which, in a multi-input multi-output (MIMO) ANC system, improved performance may be achieved by performing equalization amongst the channels to keep the coupling effects between the channels unchanged.

SUMMARY

In a disclosed embodiment, a method of multi-channel active cancellation of undesired acoustic noise in a working environment comprises operating a random noise generator to feed noise a secondary disturbance to at least two control speakers; using at least two microphones to measure responses to the secondary disturbance; forming a finite impulse response of an estimated secondary path transfer function matrix (SPTFM) based upon the microphone responses; taking a Fast Fourier Transform of the finite impulse response of the estimated SPTFM to find a frequency response of the estimated SPTFM; calculating a mean magnitude of a main path of each column of the frequency response of the estimated SPTFM; dividing each column of the frequency response of the estimated SPTFM by its respective main path mean magnitude; multiplying the matrix resulting from the dividing step by a reference value to obtain a frequency response of the virtual SPTFM; generating a reference signal correlated with the undesired acoustic noise; filtering the reference signal with the frequency response of the virtual SPTFM to produce a filtered reference signal; taking an inverse Fast Fourier Transform of the frequency response of virtual SPTFM to get the finite impulse response of the virtual SPTFM; applying a filtered-x least mean squares algorithm to the filtered reference signal and to an error feedback signal from the at least two microphones and using the result to update coefficients of an adaptive filter; filtering the reference signal using the adaptive filter to produce a cancellation signal; using the cancellation signal to drive the control speakers and thereby cancel the undesired noise correlated with the reference signal; and recursively adjusting the adaptive filter with the filtered reference signal and the error feedback signal.

In another disclosed embodiment, a method for modeling a secondary path for an active noise control system having at least two input signals and at least two output signals comprises forming an estimated secondary path transfer function matrix (SPTFM) based upon the system outputs; taking a Fast Fourier Transform of the estimated SPTFM; calculating a mean magnitude of a main path of each column of the estimated SPTFM; and dividing each column of the estimated SPTFM by its respective main path mean magnitude; multiplying by a reference value to obtain a virtual SPTFM.

BRIEF DESCRIPTION OF THE DRAWINGS

Embodiments of the present invention will now be described, by way of example only, with reference to accompanying drawings in which:

FIG. 6*a* is a graph comparing the magnitude of transfer functions from secondary sources to error sensors $S_{11}$ and $S_{21}$;

FIG. 6*b* is a graph comparing the magnitude of transfer functions from secondary sources to error sensors $S_{22}$ and $S_{12}$;

FIG. 7*a* is a graph comparing virtual secondary path transfer functions $S_{11}^e$ and $S_{21}^e$ using the improved virtual secondary path algorithm;

FIG. 7*b* is a graph comparing virtual secondary path transfer functions $S_{22}^e$ and $S_{12}^e$ using the improved virtual secondary path algorithm;

FIG. 8*a* is a graph comparing ANC results between a conventional EE-FxLMS algorithm and the disclosed virtual secondary path algorithm using microphone 1 in the system of FIG. 5;

FIG. 8*b* is a graph comparing ANC results between a conventional EE-FxLMS algorithm and the disclosed virtual secondary path algorithm using microphone 2 in the system of FIG. 5;

FIG. 9*a* is a graph comparing ANC results between the improved virtual secondary path algorithm with and without turning point using Microphone 1; and FIG. 9*b* is a graph comparing ANC results between the improved virtual secondary path algorithm with and without turning point using Microphone 2.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The disclosed method implements a channel equalization (CE) virtual secondary path algorithm, which is meant to improve the performance of multiple-channel active noise control system with either single-reference or multiple-reference signals. In practice, because of the arrangement and sensitivities of the actuators (speakers), transducers (microphones) and physical environment, the magnitude of the main secondary path transfer functions can be very different from each other. This difference will cause difficulty in the overall convergence of the algorithm, which will result in minimal attenuation at some of the channels. The disclosed channel equalization virtual secondary path algorithm is designed to tackle this difficulty by equalizing the mean magnitude of the main secondary paths and adjusting other secondary paths correspondingly to keep the coupling effects among the channels unchanged. The performance of the disclosed algorithm is validated by a single-reference two-input two-output active powertrain noise control system.

Figure 1:
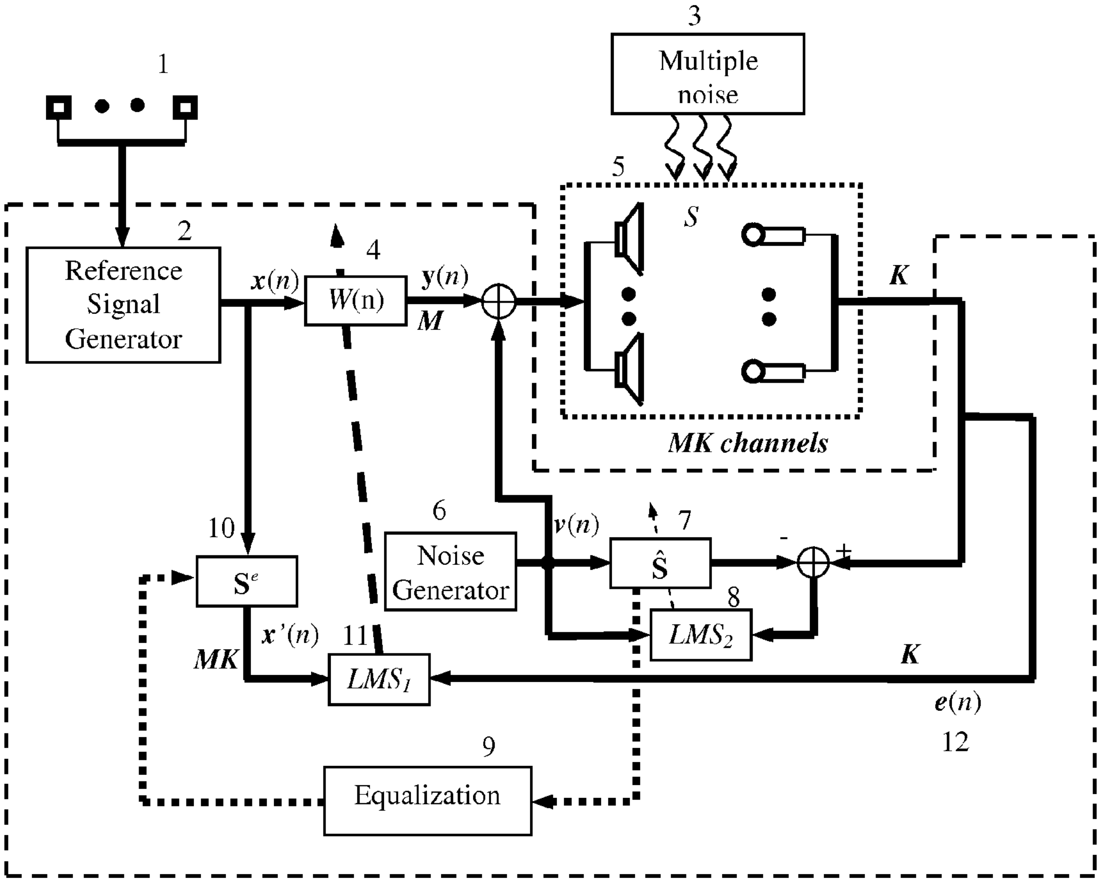
FIG. 1 is a schematic block diagram showing a basic configuration of a general multi-channel ANC system using channel equalization.
Figure 3:
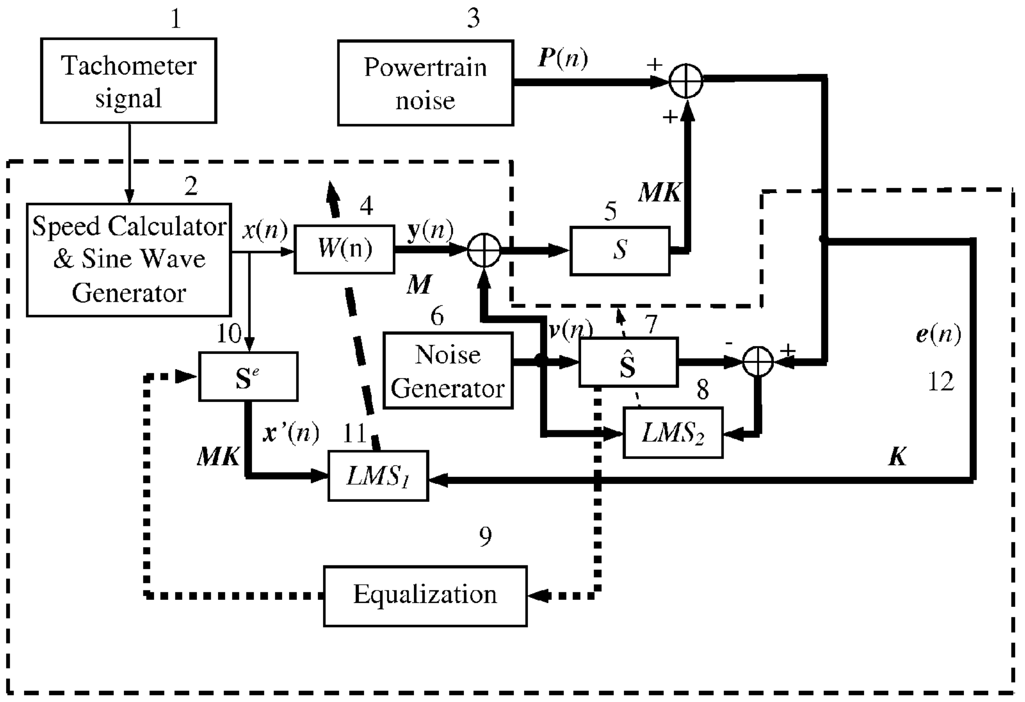
FIG. 3 is a schematic block diagram showing an automotive vehicle powertrain application of multi-channel ANC system with channel equalization.

FIG. 1 is a block diagram of a multiple-reference, multiple-input multiple-output (MIMO) system using channel equalization as applied to a general, multi-channel ANC system. FIG. 3 is a similar block diagram, but as applied to an ANC system used to cancel the powertrain noise in an automotive vehicle. One or more reference sensors 1 may be, for example, tachometer sensors (reading the RPM of an engine, motor, generator, or other rotating machine), accelerometers (reading vibrations in a vehicle suspension system, for example), or microphones (detecting noise signals of any kind). Reference signal generator 2 generates a reference signal x(n) according to the inputs from the reference sensors 1. In the application of vehicle powertrain noise control, for example, a tachometer signal captures the rotational speed of an engine or drive shaft and the reference signal may be a combination of several targeted rotational orders of engine crankshaft (or/and drive shaft) speed can be generated using a sine wave generator based on the calculated speed. In the typical case, tachometer signal or equivalent one is used to generate harmonics as the reference for harmonic response control and the sound signal is used directly as the reference.

Noise sources (block 3) are the noises in the operating environment that are to be cancelled by the ANC system. For example, noise sources in an automotive environment may be associated with the engine, other portions of the driveline, suspension, road induced noise, etc.

Adaptive filters W(n) (block 4) are used to filter the reference signal to generate signals driving the control speakers. M is the total number of control speakers, so there are also M driving signals. Filter coefficients are automatically and recursively adjusted through FX-LMS control algorithm (block 11), as will be discussed further below.

A secondary path transfer function matrix s (block 5) relates the control signals (sent to speakers M) to the sound pressure responses (measured by the error microphones K), $$s = \begin{bmatrix} s_{11} & \cdots & s_{1M} \\ \vdots & \ddots & \vdots \\ s_{K1} & \cdots & s_{KM} \end{bmatrix}_{K \times M}$$

where $s_{km}$ represents the finite impulse response of the transfer function from the m-th speaker to k-th error microphone. K is the total number of error transducers.

A random noise generator (block 6) feeds a secondary disturbance v(n) to the control speakers. Secondary disturbance v(n) is uncorrelated with the control input signal x(n) in order to allow the finite impulse response of an estimated secondary path transfer function matrix $\hat{s}$.

The finite impulse response of an estimated secondary path transfer function matrix $\hat{s}$ (see block 7) is defined as:

$$\hat{s} = \begin{bmatrix} \hat{s}_{11} & \cdots & \hat{s}_{1M} \\ \vdots & \ddots & \vdots \\ \hat{s}_{K1} & \cdots & \hat{s}_{KM} \end{bmatrix}_{K\times M}$$

The finite impulse response of an estimated secondary path transfer function matrix $\hat{s}$ is constructed using system identification of LMS algorithm (block 8).

In a process known as channel equalization (CE) (block 9), the mean amplitudes of primary elements of the estimated Secondary Path Transfer Function Matrix are equalized and other elements are adjusted correspondingly to keep the coupling effect unchanged. CE may be performed only in the frequency range of interest.

The transfer function yielded by the CE process is referred to as a virtual secondary path transfer function $s^e$ (block 10): Equalized secondary path transfer function for filtered-x least mean square algorithm (FxLMS).

$$s^e = \begin{bmatrix} s^e_{11} & \cdots & s^e_{1M} \\ \vdots & \ddots & \vdots \\ s^e_{K1} & \cdots & s^e_{KM} \end{bmatrix}_{K\times M}$$

Here, $s^e$ is used to filter the reference signal x(n) to yield the filtered reference signal x'(n).

Error feedback signals e(n) (block 12) are the error signals sensed by each of the K transducers (error microphones, in this example).

Figure 2:
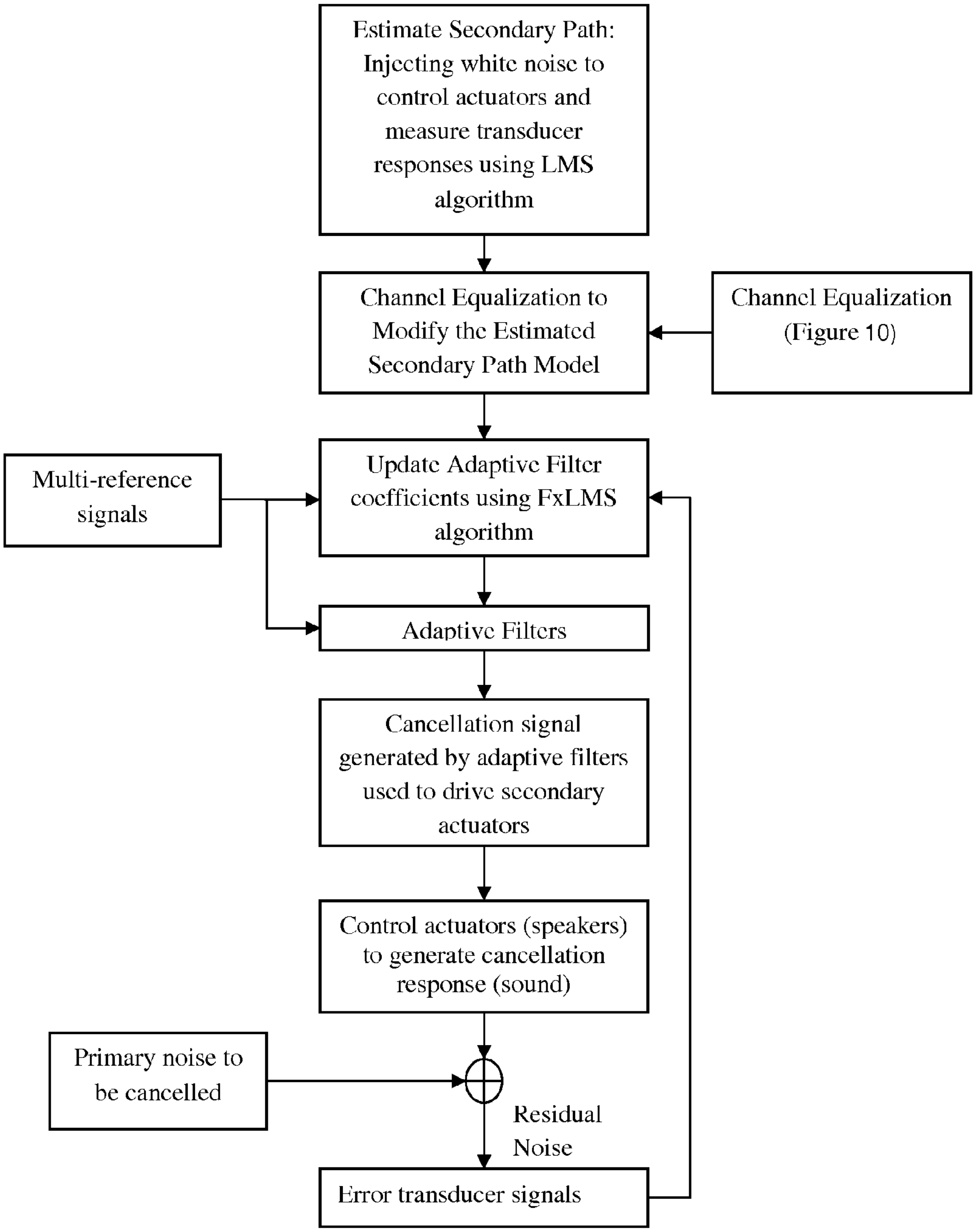
FIG. 2 is a flow chart showing an ANC method using channel equalization.
Figure 4:
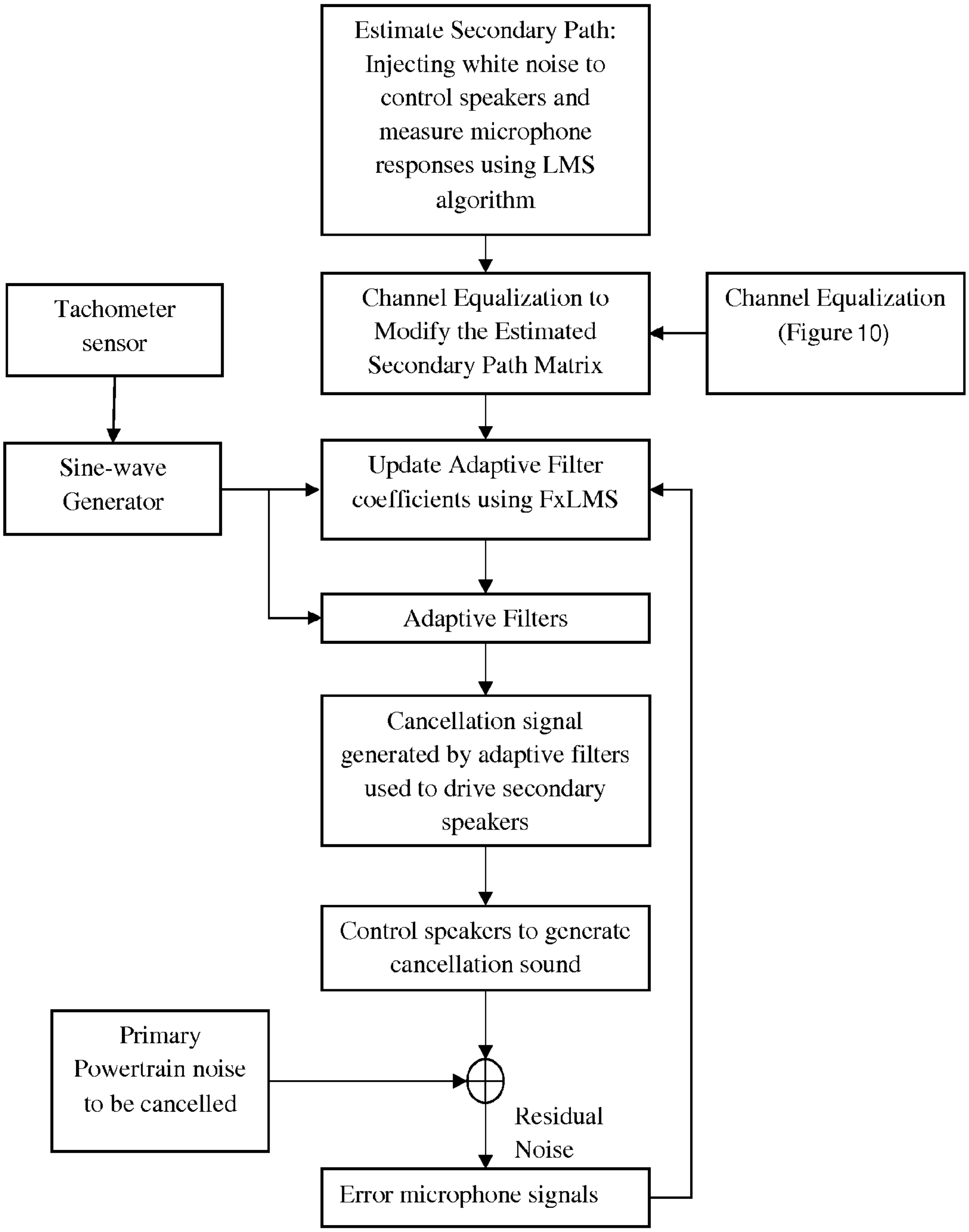
FIG. 4 is a flow chart showing an ANC method using channel equalization as used in an automotive vehicle powertrain.

FIGS. 2 and 4 illustrate the functioning of the system described above in the form of a method flow chart, with the method steps corresponding to the blocks of FIGS. 1 and 3 respectively.

A single reference signal x(n) may be used for all the M adaptive filters, or multiple reference signals may be used.

In the vehicle powertrain example, the frequencies of the reference signal can be calculated by using the engine crankshaft speed data estimated from the measured raw tachometer signals. Then, assuming x(n) is a superposition of a series of pure sine waves, it can be expressed as:

$$x(n) = \sum_{i=1}^{N} a_i \sin(2\pi n f_i / f_s) \qquad 1)$$

where $a_i$ is the amplitude of the $i^{th}$ order, $f_i$ is the frequency of the $i^{th}$ order, and $f_s$ is the sampling rate. With the information contained in the above equation, it is then possible to target the specific harmonics for tuning.

The objective of controller design is to minimize the sum of the squares of residual noise terms measured by K error sensors. Accordingly, the adaptive filter coefficients update in time domain can be expressed as:

$$w_m(n+1)=w_m(n)+\mu x_{km}(n)e_k(n) \qquad 2)$$

where $w_m(n)\equiv[w_{m,0}(n)\ w_{m,1}(n)\ \ldots\ w_{m,L-1}(n)]^T$, m=1, 2, . . . , M, M represents the number of adaptive filters; $e_k$ (n) is the residual noise at the $k^{th}$ error sensor; L is the adaptive filter length; and $x'_{km}$ (n) is the filtered reference signal calculated by the convolution of the $x(n)\equiv[x(n)\ x(n-1)\ \ldots\ x(n-L+1)]^T$ and $\hat{s}_{km}$ that is the finite impulse response of the estimate of the secondary path $s_{km}$ from the $m^{th}$ secondary source to the $k^{th}$ error sensor. The estimate of the secondary path is generated by injecting a secondary disturbance (for example, a small amount of white noise) v(n) through the control input speaker. By using a secondary disturbance v(n) that is uncorrelated with the control input signal u(n), the secondary path can be updated using the standard LMS algorithm. This is called off-line modeling (also known as off-line system identification) technique.

P(n) represents the powertrain noise in the automotive example. The convergence speed of the algorithm is determined by the eigenvalue spread of the autocorrelation matrix of the filtered reference signal x'(n) and can be written as:

$$R=E[x'^T(n)x'(n)] \qquad 3)$$

where E[ ] represent the statistical expectation operator. Accordingly, the eigenvalue spread denoted by ρ can be defined as the ratio between the largest eigenvalue and smallest eigenvalue of the autocorrelation matrix R, $$\rho = \frac{\lambda_{max}}{\lambda_{min}} \qquad 4)$$

Alternatively, the algorithm shown in equation (2) can be expressed in the frequency domain as:

$$W(n+1,\omega)=W(n,\omega)+\mu X'^H(n,\omega)E(n,\omega) \qquad 5)$$

where the operation $[\cdot]^H$ indicates the Hermitian transpose, and $$E(n,\omega)=[E_1(n,\omega)E_2(n,\omega)\ldots E_K(n,\omega)]^T \qquad 6)$$

$$W(n,\omega)=[W_1(n,\omega)W_2(n,\omega)\ldots W_M(n,\omega)]^T \qquad 7)$$

The filtered reference matrix X'(n,ω) is a K×M matrix defined by:

$$X'(n,\omega) = \begin{bmatrix} X'_{11}(n,\omega) & X'_{12}(n,\omega) & \ldots & X'_{1M}(n,\omega) \\ X'_{21}(n,\omega) & X'_{22}(n,\omega) & \ldots & X'_{2M}(n,\omega) \\ \vdots & \vdots & & \vdots \\ X'_{K1}(n,\omega) & X'_{K2}(n,\omega) & \ldots & X'_{KM}(n,\omega) \end{bmatrix} \qquad 8)$$

where $X'_{km}(n,\omega)=\hat{S}_{km}(n,\omega)X(n,\omega)$. Here, X (n,ω) is the reference signal of x(n) in frequency domain, and $\hat{S}_{km}(n,\omega)$ is the frequency response of the estimate of the secondary path transfer function from the $m^{th}$ secondary source to the $k^{th}$ error sensor in frequency domain. Equation (7) can be expanded as:

$$X'(n,\omega) = \begin{bmatrix} \hat{S}_{11}X & \hat{S}_{12}X & \ldots & \hat{S}_{1M}X \\ \hat{S}_{21}X & \hat{S}_{22}X & \ldots & \hat{S}_{2M}X \\ \vdots & \vdots & & \vdots \\ \hat{S}_{K1}X & \hat{S}_{K2}X & \ldots & \hat{S}_{KM}X \end{bmatrix} \qquad 9)$$

-continued $$X'(n,\omega)=\begin{bmatrix}\hat{S}_{11} & \hat{S}_{12} & \dots & \hat{S}_{1M}\\ \hat{S}_{21} & \hat{S}_{22} & \dots & \hat{S}_{2M}\\ \vdots & \vdots & & \vdots\\ \hat{S}_{K1} & \hat{S}_{K2} & \dots & \hat{S}_{KM}\end{bmatrix}\begin{bmatrix}X & 0 & \dots & 0\\ 0 & X & \dots & 0\\ \vdots & \vdots & & \vdots\\ 0 & 0 & \dots & X\end{bmatrix}=\hat{S}X \qquad 10)$$

It may be noted that (n,ω) has been omitted from Equations (8) and (9) for simplification. Then, Equation (3) can be written in frequency domain as $$R(\omega)=E[X'^H(n,\omega)X'(n,\omega)]=E[X^H\hat{S}^H\hat{S}X] \qquad 11)$$

The power spectrum matrix R(ω) is an M×M matrix at each frequency bin ω. Therefore, the convergence behavior at the frequency bin ω can be clearly observed. The convergence properties are still determined by the eigenvalue spread of R(ω) at each frequency bin ω. Accordingly, Equation (4) can be expressed in the frequency domain as:

$$\rho_1=\frac{\lambda_{max}(\omega)}{\lambda_{min}(\omega)} \qquad 12)$$

where $\lambda_{max}$ and $\lambda_{min}$ are the largest and smallest eigenvalues at the frequency bin ω, respectively. It is well known that a smaller $\rho_1$ can achieve a faster convergence.

Eigenvalue equalization may optionally be applied along with channel equalization to improve performance of a system.

Observing the convergence over the whole frequency range, the eigenvalue spread can be revised as:

$$\rho_2=\frac{\max\{\lambda_{max}(\omega)\}}{\min\{\lambda_{min}(\omega)\}} \qquad 13)$$

where $\max\{\lambda_{max}(\omega)\}$ and $\min\{\lambda_{min}(\omega)\}$ represent the maximum and minimum eigenvalues over the entire frequency range of interest.

Hence, to study the convergence property of the system, we calculate all eigenvalues of autocorrelation matrix R(ω). This will cause a heavy computational burden especially when the length of the control filter is long. Instead of calculating the eigenvalues of the matrix R(ω), we can evaluate the convergence speed approximately by using the determinant spread of R(ω) over the entire frequency range of interest as:

$$\rho_3=\frac{\max\{|R(\omega)|\}}{\min\{|R(\omega)|\}} \qquad 14)$$

where |R(ω)| is the determinant of matrix R(ω), which can be expressed as:

$$|R(\omega)|=E[|X(\omega)|^2]|\hat{S}^H(\omega)\hat{S}(\omega)| \qquad 15)$$

Since the reference signal in this example is generated by a sine wave generator, we can easily set the reference signal with equal amplitude at all harmonics over the entire frequency range of interest. Hence, the power spectrum of the reference signal at each frequency bin ω will be the same. Thus, Equation (14) can be derived as:

$$\rho_3=\frac{\max\{|\hat{S}^H(\omega)\hat{S}(\omega)|\}}{\min\{|\hat{S}^H(\omega)\hat{S}(\omega)|\}} \qquad 16)$$

As noted above, to achieve faster convergence, a smaller $\rho_3$ is required. This implies that $|\hat{S}^H(\omega)\hat{S}(\omega)|$ should be as flat as possible over the entire frequency range of interest.

The eigenvalue equalization filtered-x least mean square (EE-FxLMS) algorithm may be used to flatten the magnitude response of $\hat{S}_{km}(n,\omega)$ for each secondary path in the system by modifying the magnitude in frequency domain. To maintain stability, the phase is kept unchanged. The resultant modified estimation of the secondary path is referred to as a virtual secondary path, which is expressed as $S_{km}^e$. This virtual secondary path is then used to replace the estimated model of the secondary path in the original version of the FxLMS algorithm. The algorithm applying this technique is illustrated in FIG. 1.

When the virtual secondary path is applied in the FxLMS algorithm, $|\hat{S}^H(\omega)\hat{S}(\omega)|$ in Equation (16) is replaced by $|S^{eH}(\omega)S^e(\omega)|$. In the single-input, single-output (SISO) ANC system, the determinant of $|S^{eH}(\omega)S^e(\omega)|$ becomes the power of the virtual secondary path $|S^e|^2$ from the secondary source to the error sensor. Since $S^e$ has a flat magnitude in each frequency bin, the overall convergence speed in all frequency bins is naturally improved. How the magnitude of $S^e$ is to be chosen is not a critical issue for a SISO system because the magnitude errors can be compensated by tuning the value of step size parameter. However, it is important to choose the magnitude of the virtual secondary path $S_{km}^e$ for a multiple-input, multiple-output (MIMO) system. Selection of the magnitude of the secondary path (the estimated secondary path $\hat{S}_{km}$ or the virtual secondary path $S_{km}^e$) is critical to convergence speed to each channel. In the example discussed, the multiple channel control system has identical number of control speakers and error sensors, M=K. Thus, the update equation of the i-th adaptive filter can be written as $$w_i(n+1)=w_i(n)+\mu[\hat{s}_{1i}(n)*x(n)]e_1(n)+\dots+\mu[\hat{s}_{ii}(n)*x(n)]e_i(n)+\dots+\mu[\hat{s}_{Mi}(n)*x(n)]e_M(n) \qquad 18)$$

where μ is the step size parameter and i=1, 2, . . . , M. It is apparent that that the adaptive algorithm for such a control system requires that the signal from every error sensor is used at each iteration to adjust the controller of each secondary source. Also, each error signal is weighted by corresponding estimated secondary path. The estimated secondary path transfer function matrix in frequency domain can be expressed as $$\hat{S}=\begin{bmatrix}\hat{S}_{11} & \hat{S}_{12} & \dots & \hat{S}_{1M}\\ \hat{S}_{21} & \hat{S}_{22} & \dots & \hat{S}_{2M}\\ \vdots & \vdots & & \vdots\\ \hat{S}_{M1} & \hat{S}_{M2} & \dots & \hat{S}_{MM}\end{bmatrix}_{M\times M} \qquad 19)$$

Assume that the estimated secondary path $\hat{S}_{ii}$ is the main path of the i-th column of $\hat{S}$ so that the main path of each column vectors is the diagonal element of the secondary path matrix $\hat{S}$. Main path means one control speaker (the i-th control speaker) has more influence on one error sensor (the i-th error sensor) than any other error sensors. In fact, the i-th column of $\hat{S}$ are the weights used to update the i-th adaptive filter as equation (18). Hence, the main path $\hat{S}_{ii}$ is the biggest weight for updating $w_i$. Mathematically, the mean magnitude value of $\hat{S}_{ii}$ is larger than the mean magnitude value of $\hat{S}_{k\neq i,i}$, where k=1, 2, . . . , M. $\hat{S}_{j\neq i,i}$ are coupling estimated secondary paths for the i-th channel. In practice, the magnitude of each main path mostly is not identical to each other. Without losing generality, we assume the mean magnitude value of $\hat{S}_{ii}$ is larger than the mean magnitude value of $\hat{S}_{jj}$, where j=1, 2, . . . , M, but j≠i, expressed as mean[$\hat{S}_{ii}$]>mean[$\hat{S}_{jj}$].

The extreme case of this phenomenon may be studied as follows. If mean[$\hat{S}_{ii}$]>>mean[$\hat{S}_{jj}$], because the coupling secondary paths are smaller than the main path, the adaptive filter $w_j$ will converge much slower than the adaptive filter $w_i$ by applying equation (18).

Channel equalization (CE) is applied to improve the overall convergence speed of the MIMO ANC system. The idea is to normalize the mean magnitude value of the main secondary paths of each column of the secondary path matrix $\hat{S}$ while keeping the coupling ratios between couple weights and the biggest weight unchanged. The normalization process is implemented as $$S^e = \alpha\begin{bmatrix} \frac{\hat{S}_{11}}{\text{mean}[\hat{S}_{11}]} & \frac{\hat{S}_{12}}{\text{mean}[\hat{S}_{12}]} & \cdots & \frac{\hat{S}_{1M}}{\text{mean}[\hat{S}_{MM}]} \\ \frac{\hat{S}_{21}}{\text{mean}[\hat{S}_{11}]} & \frac{\hat{S}_{22}}{\text{mean}[\hat{S}_{22}]} & \cdots & \frac{\hat{S}_{2M}}{\text{mean}[\hat{S}_{MM}]} \\ \vdots & \vdots & & \vdots \\ \frac{\hat{S}_{M1}}{\text{mean}[\hat{S}_{11}]} & \frac{\hat{S}_{M2}}{\text{mean}[\hat{S}_{22}]} & \cdots & \frac{\hat{S}_{MM}}{\text{mean}[\hat{S}_{MM}]} \end{bmatrix}_{M\times M} \tag{20}$$

Again, $S^e$ is virtual secondary path. Here, the eigenvalue equalization technique is not used to modify the secondary path, but only the proposed channel equalization technique. More specifically, the virtual secondary path found using only the channel equalization technique (without eigenvalue equalization) is referred to as the channel equalized (CE) virtual secondary path.

In equation (20), α is a reference value. It can be set to any desired value. Usually, α is set to unit value 1, or the mean magnitude of the main secondary path that has the maximum mean magnitude among all main paths from column 1 to column M. mean[$\hat{S}_{km}$] is the mean magnitude value of the secondary path $\hat{S}_{km}$ in the frequency range of interests.

For more general cases, the number of control speakers is not equal to the number of error sensors K≠M or K=M, so that the main path may be an off-diagonal element.

$$\hat{S} = \begin{bmatrix} \hat{S}_{11} & \hat{S}_{12} & \cdots & \hat{S}_{1M} \\ \hat{S}_{21} & \hat{S}_{22} & \cdots & \hat{S}_{2M} \\ \vdots & \vdots & & \vdots \\ \hat{S}_{K1} & \hat{S}_{K2} & \cdots & \hat{S}_{KM} \end{bmatrix}_{K\times M} \tag{21}$$

The first step is to find the main path of the i-th column of $\hat{S}$. Assume that $\hat{S}_i^{main}$ is the main path of the i-th column and α is a reference value. Then, we equalize the magnitude of the main path according to the reference value as $$S^e = \alpha\begin{bmatrix} \frac{\hat{S}_{11}}{\text{mean}[\hat{S}_1^{main}]} & \frac{\hat{S}_{12}}{\text{mean}[\hat{S}_2^{main}]} & \cdots & \frac{\hat{S}_{1M}}{\text{mean}[\hat{S}_M^{main}]} \\ \frac{\hat{S}_{21}}{\text{mean}[\hat{S}_1^{main}]} & \frac{\hat{S}_{22}}{\text{mean}[\hat{S}_2^{main}]} & \cdots & \frac{\hat{S}_{2M}}{\text{mean}[\hat{S}_M^{main}]} \\ \vdots & \vdots & & \vdots \\ \frac{\hat{S}_{K1}}{\text{mean}[\hat{S}_1^{main}]} & \frac{\hat{S}_{K2}}{\text{mean}[\hat{S}_2^{main}]} & \cdots & \frac{\hat{S}_{KM}}{\text{mean}[\hat{S}_M^{main}]} \end{bmatrix}_{K\times M} \tag{22}$$

In this way, the mean magnitudes of the main secondary paths of the secondary path matrix are all equalized to the reference value α. The mean magnitudes of other secondary paths in the column i are adjusted correspondently to keep the coupling effects unchanged, and they are less than α.

The above-described channel equalization technique may be combined with the eigenvalue equalization technique to achieve better performance of MIMO systems, and is particularly useful in an ANC system applied to an automotive powertrain noise application. In this case, $s^e$ still present the virtual secondary path by combined techniques, namely EE-CE virtual secondary path. The procedure is to first equalize the magnitude along frequencies of each secondary path by eigenvalue equalization technique, and next to equalize the mean magnitude along channels by the channel equalization technique.

In general, the EE-CE virtual secondary path $S^e$ can be defined as, $$S^e = \begin{bmatrix} S_{11}^{EE} & \cdots & S_{1M}^{EE} \\ \vdots & \ddots & \vdots \\ S_{K1}^{EE} & \cdots & S_{KM}^{EE} \end{bmatrix}_{K\times M}$$

Figure 5:
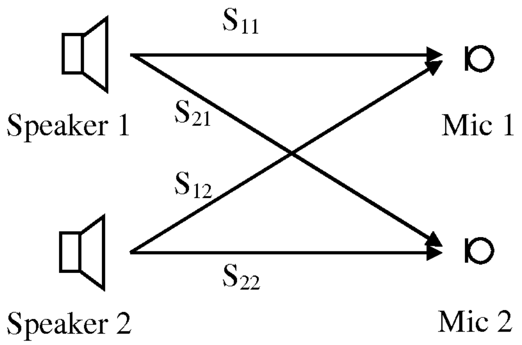
FIG. 5 is a schematic diagram of a two-input, two-output (2I2O) ANC system illustrating the secondary paths.

In the disclosed example, the method is carried out using a two-input two output (2I2O) ANC system as shown in FIG. 5. After applying eigenvalue equalization, the virtual secondary path becomes $$S^e = \begin{bmatrix} S_{11}^{EE} & S_{12}^{EE} \\ S_{21}^{EE} & S_{22}^{EE} \end{bmatrix}_{2\times 2} \tag{23}$$

We assume that the $\hat{S}_{11}$ and $\hat{S}_{22}$ are the main paths of the first and second column of secondary path matrix $\hat{S}$, respectively, and the mean[$\hat{S}_{22}$]>mean[$\hat{S}_{11}$]. By applying a channel equalization technique, the main paths of the virtual secondary path were normalized to the mean magnitude value of $\hat{S}_{22}$, which mean the reference value α=mean[$\hat{S}_{22}$]. Thus, the virtual secondary path becomes $$S^e = \alpha\begin{bmatrix} \frac{S_{11}^{EE}}{\text{mean}[\hat{S}_{11}]} & \frac{S_{12}^{EE}}{\text{mean}[\hat{S}_{22}]} \\ \frac{S_{21}^{EE}}{\text{mean}[\hat{S}_{11}]} & \frac{S_{22}^{EE}}{\text{mean}[\hat{S}_{22}]} \end{bmatrix}_{2\times 2} \tag{24}$$

For example, the estimated secondary path transfer functions for a two-input, two-output ANC system, $\hat{S}_{11}$, $\hat{S}_{12}$, $\hat{S}_{21}$, and $\hat{S}_{22}$, were experimentally obtained on the test vehicle. The results of this are shown in FIG. 6. The two control speakers may be located in the front left and right passenger doors, respectively. The two error microphones are placed adjacent the ceiling of vehicle over driver's and passenger's head positions, respectively. The secondary path transfer functions were modeled by injecting white random noise to the control speakers and measuring the responses of the error microphones.

All four secondary path transfer functions were modeled using a 256-tap finite impulse response (FIR) filter by least mean square (LMS) algorithm. By applying the EE-CE virtual secondary path as equations (23) and (24), four virtual secondary paths are presented in FIG. 7. It is seen that the magnitude of $S_{11}{}^{e}$ is equal to magnitude of $S_{22}{}^{e}$, and the ratios of $S_{21}{}^{e}/S_{11}{}^{e}$ and $S_{12}{}^{e}/S_{22}{}^{e}$ stay as the original ratios of $S_{21}/S_{11}$ and $S_{12}/S_{22}$ in the frequency range of interest. The frequency range of interest here is 50 Hz to 300 Hz.

Figure 10:
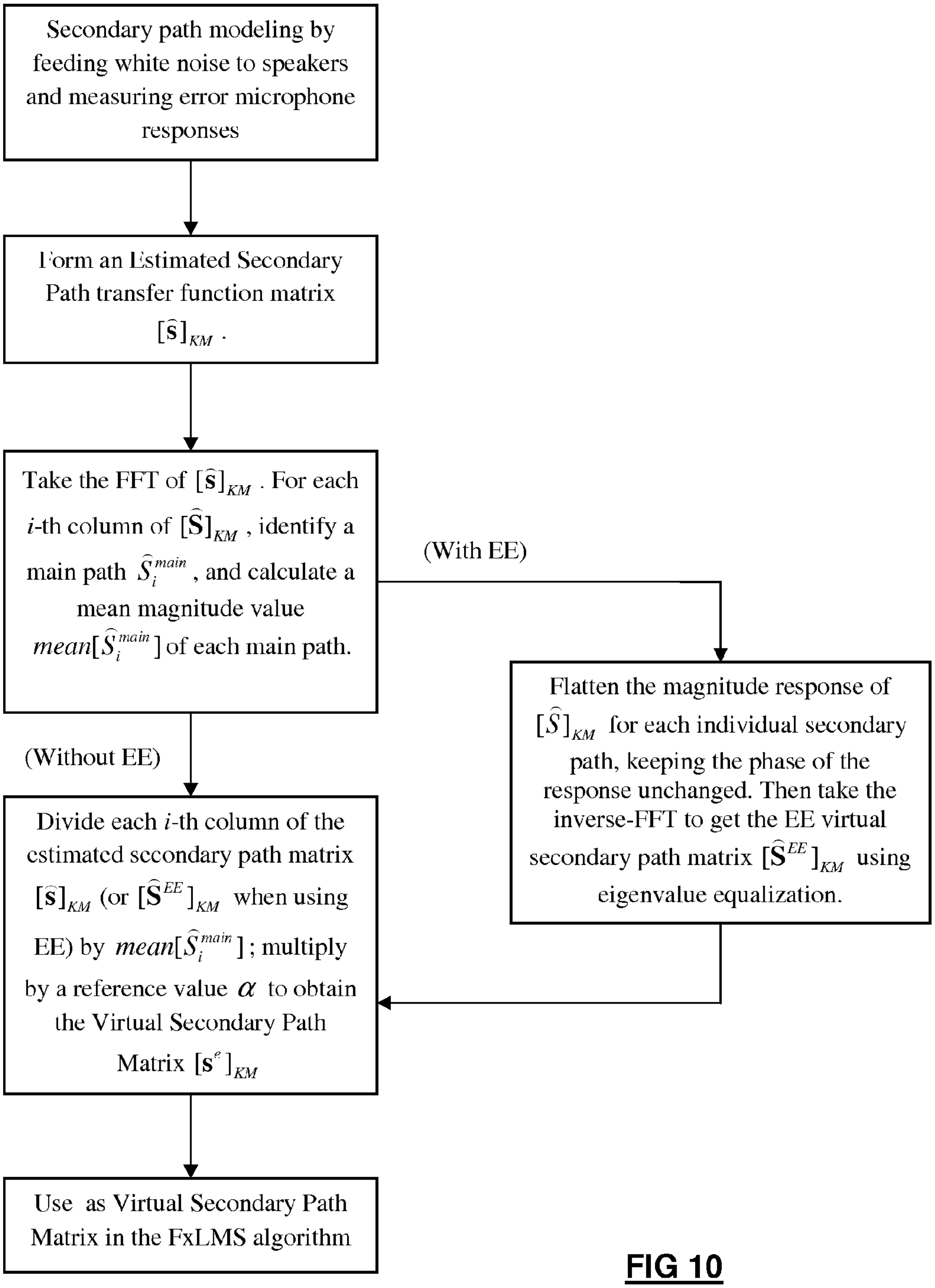
FIG. 10 is a flow chart showing the Channel Equalization procedure.

FIG. 10 shows, in the form of a flow chart, details of the channel equalization process described above. In FIG. 10, lowercase letter such as $[\hat{s}]_{KM}$ represents the finite impulse response of the secondary path transfer function matrix, while capital letter such as $[\hat{S}]_{KM}$ represents the frequency response of the secondary path transfer function matrix.

The method described herein can be examined using a mathematical simulation and analysis program such as MATLAB/Simulink. The baseline signals of the powertrain noise along with tachometer signal are recorded during testing of an actual experimental vehicle, during which the engine speed ramps up from 1000 rpm to 5500 rpm within 10 seconds. The four secondary path transfer functions for a two-input, two-output ANC system, $S_{11}$, $S_{12}$, $S_{21}$, and $S_{22}$, were experimentally obtained on the test vehicle as shown in FIGS. 6*a,b*. The estimates of the secondary path may be modeled using a 256-tap finite impulse response (FIR) filter.

For demonstration purpose, the purpose of these simulations is to reduce the response of the $1.5^{th}$, $2^{nd}$, and $3^{rd}$ order as much as possible. By applying the EE-CE virtual secondary path algorithm, four virtual secondary paths are presented in FIGS. 7*a* and 7*b*. It is seen that the magnitude of $S_{11}{}^{e}$ is equal to the magnitude of $S_{22}{}^{e}$, and the ratios of $S_{21}{}^{e}/S_{11}{}^{e}$ and $S_{12}{}^{e}/S_{22}{}^{e}$ stay as the primary ratios of $S_{21}/S_{11}$ and $S_{12}/S_{22}$ in the frequency range of interest. The frequency range of interest here is 50 Hz to 300 Hz.

FIGS. 8*a* and 8*b* show the simulation results for sound reduction at $3^{rd}$ order, which is the cylinder firing order of the engine being analyzed in this example. FIG. 8*a* is the control result at the first microphone of the two-input system of FIG. 5, and FIG. 8*b* is the control result at second microphone. The step size $\mu$ for each implementation is set to the largest value for which stability is still maintained.

The solid curves in FIGS. 8*a* and 8*b* are the original response of the powertrain noise at microphone 1 and microphone 2, respectively. The dashed curves are the sound pressure response after the control is activated using the EE virtual secondary path algorithm. The dotted curves show the control result of the implementation of the channel equalization virtual secondary path algorithm.

It can be seen that the controlled response at microphone 1 applying the EE virtual secondary path algorithm (dashed curve in FIG. 8*a*) does not show significant reduction. However, the reduction at microphone 2 depicted by the comparison of the dashed and solid curves in FIG. 8*b* can be clearly seen. Also, it is apparent that the EE virtual secondary path algorithm yields an unbalanced noise reduction result between microphone 1 and microphone 2. This is because the magnitude of $S_{22}$ is much higher than that of $S_{11}$, and the original noise response at microphone 2 is higher than the noise response at microphone 1. On the other hand, from the results represented by the dotted curve in FIGS. 8*a,b*, it can be seen that the EE-CE (combined eigenvalue equalization and channel equalization) virtual secondary path algorithm yields a much more balanced noise reduction result between the two different microphones. Also, the EE-CE algorithm produces a greater level of attenuation.

The performance can be further improved by adding a turning point where the step size is changed. The turning point is determined experimentally based on the specific case under consideration. In this case, 2400 rpm has been chosen as a turning point. FIGS. 9*a* and 9*b* shows the simulation results using the channel equalization virtual secondary path with and without using the turning point for microphone 1 and microphone 2, respectively. In FIGS. 9*a,b*, the step size of the dotted curve is 1.6 times larger when the speed is below than 2400 rpm and is the same as the dashed curve one when the speed is higher than 2400 rpm. It can be clearly seen that the dotted curve is able to achieve more reduction when the engine speed is lower than 2400 rpm by using a larger step size.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of a multi-channel active cancellation of undesired acoustic noise in a working environment comprising:

operating a random noise generator to feed a secondary disturbance to at least two control speakers;

using at least two microphones to measure responses to the secondary disturbance;

forming a finite impulse response of an estimated secondary path transfer function matrix (SPTFM) $[\hat{s}]_{KM}$ based upon the microphone responses;

taking a Fast Fourier Transform of the finite impulse response of the estimated SPTFM $[\hat{s}]_{KM}$ to find a frequency response of the estimated SPTFM $[\hat{S}]_{KM}$;

calculating a mean magnitude of a main path of each column of the frequency response of the estimated SPTFM $[\hat{S}]_{KM}$;

dividing each column of the frequency response of the estimated SPTFM$[\hat{S}]_{KM}$ by its respective main path mean magnitude;

multiplying the matrix resulting from the dividing step by a reference value to obtain a frequency response of a virtual SPTFM$[S^{e}]_{KM}$;

generating a reference signal correlated with the undesired acoustic noise;

filtering the reference signal with the frequency response of the virtual SPTFM $[S^{e}]_{KM}$ to produce a filtered reference signal;

applying a filtered-x least mean squares algorithm to the filtered reference signal and to an error feedback signal from the at least two microphones and using the result to update coefficients of an adaptive filter;

filtering the reference signal using the adaptive filter to produce a cancellation signal;

using the cancellation signal to drive the control speakers and thereby cancel the undesired acoustic noise correlated with the reference signal; and recursively adjusting the adaptive filter with the filtered reference signal and the error feedback signal.

2. The method of claim 1 further comprising performing an eigenvalue equalization in conjunction with the channel equalization, the eigenvalue equalization comprising:

flattening a magnitude of each secondary path of the frequency response of the estimated SPTFM $[\hat{S}]_{KM}$;

taking the inverse-fast-Fourier-transform of the flattened frequency response of the estimated SPTFM to yield an equalized SPTFM $[\hat{s}^{EE}]_{KM}$; and performing the dividing and multiplying steps on the equalized modified SPTFM $[\hat{S}^{EE}]_{KM}$.

3. The method of claim 1 wherein the reference value used in the multiplying step is the mean magnitude of the main secondary path having a maximum mean magnitude among all main paths.

4. The method of claim 1 wherein the undesired acoustic noise results from operation of a vehicle powertrain, and the reference signal is based on a tachometer monitoring a rotational speed of a component of the powertrain.

* * * * *

UNITED STATES PATENT AND TRADEMARK OFFICE

CERTIFICATE OF CORRECTION

PATENT NO. : 8,600,069 B2
APPLICATION NO. : 13/071712
DATED : December 3, 2013
INVENTOR(S) : Ming-Ran Lee et al.

It is certified that error appears in the above-identified patent and that said Letters Patent is hereby corrected as shown below:

ON THE TITLE PAGE

Delete:
"(73) Assignee: Ford Global Technologies, LLC, Dearborn MI (US)"

and insert

-- (73) Assignee: Ford Global Technologies, LLC Dearborn MI (US)
University of Cincinnati, Cincinnati OH (US) --.

Signed and Sealed this
Thirteenth Day of October, 2015

Michelle K. Lee

Michelle K. Lee
*Director of the United States Patent and Trademark Office*